United States Patent [19]

Pastorello

[11] Patent Number: 5,419,177
[45] Date of Patent: May 30, 1995

[54] REFRIGERANT GAS CONTAMINATION DETECTOR KIT

[76] Inventor: John Pastorello, 2919 Treeview, Fullerton, Calif. 92635

[21] Appl. No.: 217,551

[22] Filed: Mar. 25, 1994

[51] Int. Cl.⁶ .............................................. G01N 3/00
[52] U.S. Cl. ..................................... 73/23.4; 62/127; 73/29.01
[58] Field of Search ................. 73/29.01, 29.05, 31.03, 73/863.85, 23.42; 62/127

[56] References Cited

U.S. PATENT DOCUMENTS

| | | | |
|---|---|---|---|
| 4,803,843 | 2/1989 | Otto | 62/85 |
| 4,866,994 | 9/1989 | Baker | 62/127 |
| 5,071,768 | 12/1991 | Klodowski | 436/39 |
| 5,345,774 | 9/1994 | Mount | 62/127 |

*Primary Examiner*—Richard E. Chilcot, Jr.
*Assistant Examiner*—Max H. Noori

[57] ABSTRACT

A method for determining the amount of a contaminant in a refrigerant gas under pressure and the detector tube and tube holding assembly. The method involves preparing a predetermined length of refrigerant hose and connecting a pressure gauge to an exit end of the hose. The entrance to the hose is connected to a sealed detector tube which is held in a fitting which connects to conventional refrigerant hose. This fitting is connected at its other end to a source of refrigerant gas under pressure to be tested. The gas is allowed to pass through the detector tube into the known length of empty tube until the pressure gauge reaches a predetermined value depending upon the refrigerant gas to be tested. This causes a known volume of gas to pass through the detector tube and the detector tube changes color and the distance that the color change has taken place is a measure of the contaminant. Different detector tubes are used for different contaminants.

6 Claims, 3 Drawing Sheets

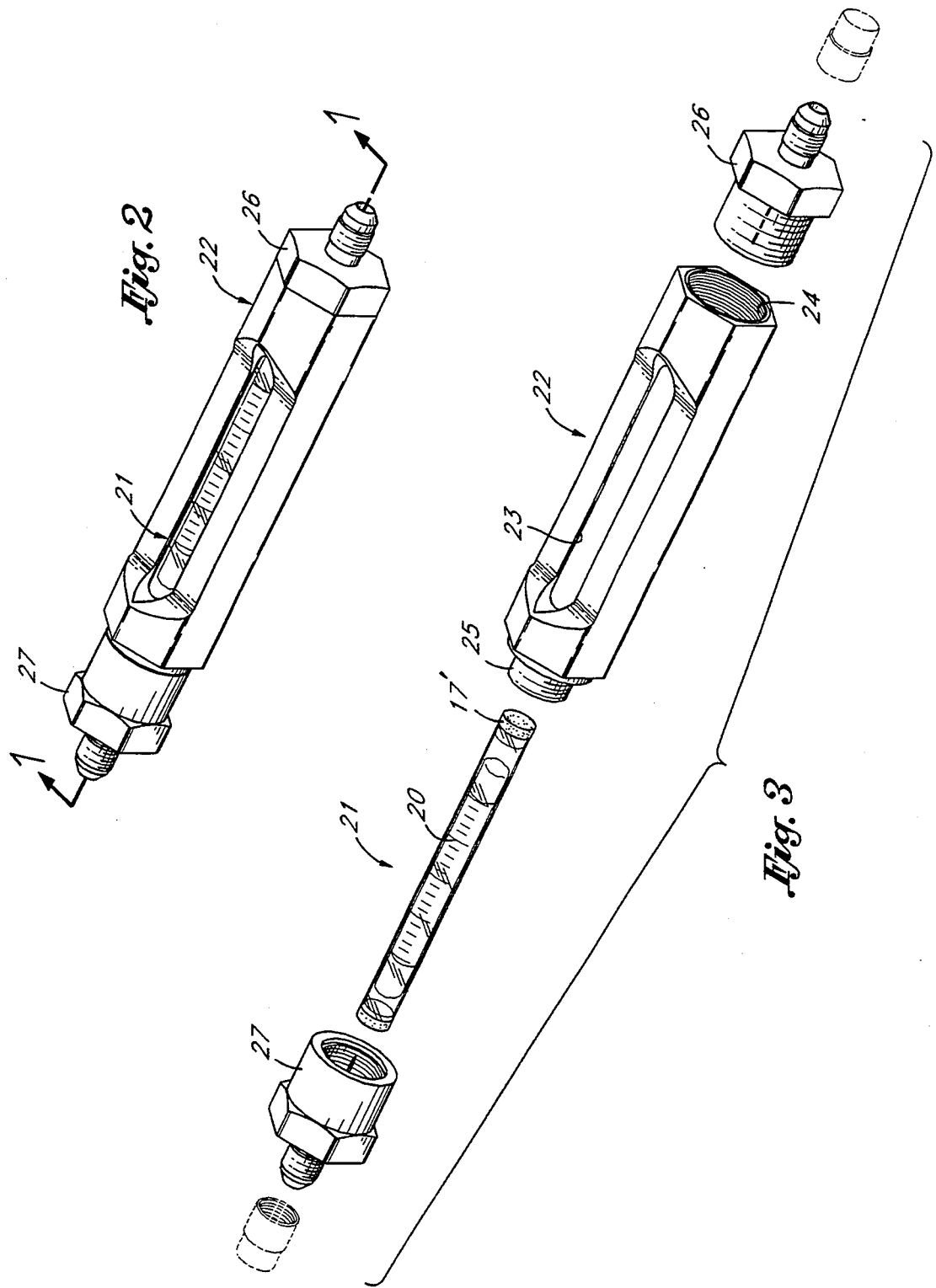

REFRIGERANT GAS CONTAMINATION DETECTOR KIT

BACKGROUND OF THE INVENTION

The field of the invention is refrigerant system servicing and the invention relates more particularly to a method and apparatus for determining contaminants in a refrigerant gas.

Since refrigerant gases can become contaminated with contaminants such as water or acid which contaminants tend to degrade the metal components of the refrigerant system, it is important to detect these contaminants as soon as possible to minimize the damage done to the system. Various methods have been used to do this, such as those shown in U.S. Pat. Nos. 5,071,768 and 4,923,806. Such systems, however, are cumbersome and expensive to use. Apparatus for testing low pressure refrigerant gas is shown in U.S. Pat. No. 4,803,843. Other patents showing gas testing systems are disclosed in U.S. Pat. Nos. 3,544,276; 4,014,216; and 4,071,319.

It is important that a device and method be available which device is portable, easy to use and relatively foolproof. There are numerous new refrigerant gases and some prior art methods that are useful for a particular refrigerant gas in most cases is not useful with a different refrigerant gas.

Recently, the Air Condition and Refrigerant Institute (ARI) has established threshold limit values for the allowable amount of contamination in refrigerant gas. This is in response to laws that prohibit venting or the release of spent refrigerants into the atmosphere. Such refrigerants are being recovered, reclaimed or recycled into external tanks or cylinders. In order to assure that the collected gas is suitable for reuse, the purity of that gas must be determined. For example, the limit value of moisture in refrigerants must not exceed 10.0 ppm, and for acid, not greater than 1.0 ppm. The present state of knowledge does not permit field sampling to such a high order of sensitivity.

SUMMARY OF THE INVENTION

It is the object of the present invention to provide a portable testing unit which may be easily used in the field and will provide a high order of sensitivity for the detection of moisture and acid.

The present invention is for a method for making a detector tube for determining the amount of a specific contaminant in a group of commonly used refrigerant gases. The present invention is also for the apparatus of carrying out such determination. The method involves sealing a known detector material in a sealed transparent tube, the detector material (or reactive media) being sensitive to a known contaminant. Next, a known volume of a pure sample of a particular refrigerant gas is transferred to a container and this pure sample is contaminated with a known contaminant, such as water or acid, with which the media in the detector tube will react. Next a flow path is created between the contaminated sample and the detector tube. The contaminated sample is allowed to reach equilibrium between its vapor phase and its liquid phase after which the gaseous or vapor phase is permitted to pass through the transparent tube until the detector material has reacted a predetermined distance along the detector tube. Next, the amount of gas required to cause the detector material to react a predetermined distance is weighed and the same procedure is carried out for each commonly used refrigerant material.

The detector tube holder of the present invention has a slotted central receptacle threaded at each end and has an elongated passageway. A hypodermic needle, having a sharpened end is supported adjacent the inlet and outlet of the slotted receptacle. When a detector tube having rubber ends, a transparent central portion and a detector material therein is placed in the elongated passageway of the slotted central receptacle, the rubber ends may be pierced by the hypodermic needles to provide a flow path for refrigerant gases. When a known volume of gas has passed therethrough the distance at which the detector material has reacted and changed color will provide a measure of the amount of contamination.

BRIEF DESCRIPTION OF THE DRAWINGS

FIG. 2 is a perspective view of the detector tube holding assembly of FIG. 1.

FIG. 3 is an exploded perspective view of the detector tube holding assembly and detector tube of FIG. 2.

DESCRIPTION OF THE PREFERRED EMBODIMENTS

Figure 1:
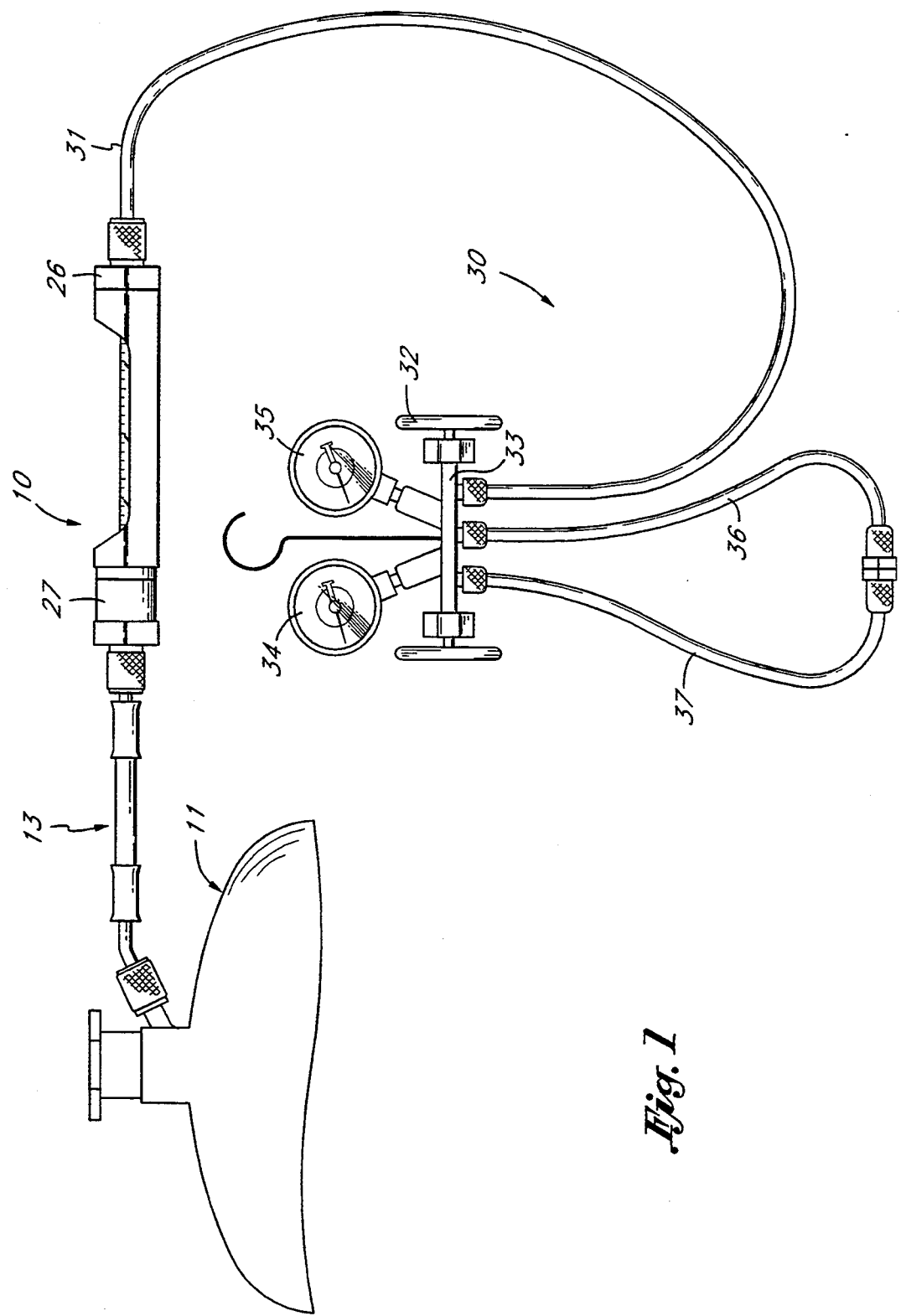
FIG. 1 is a side view of a tank filled with refrigerant to be tested connected to a slotted receptacle which has an exit hose attached to a pressure gauge assembly.
Figure 4:
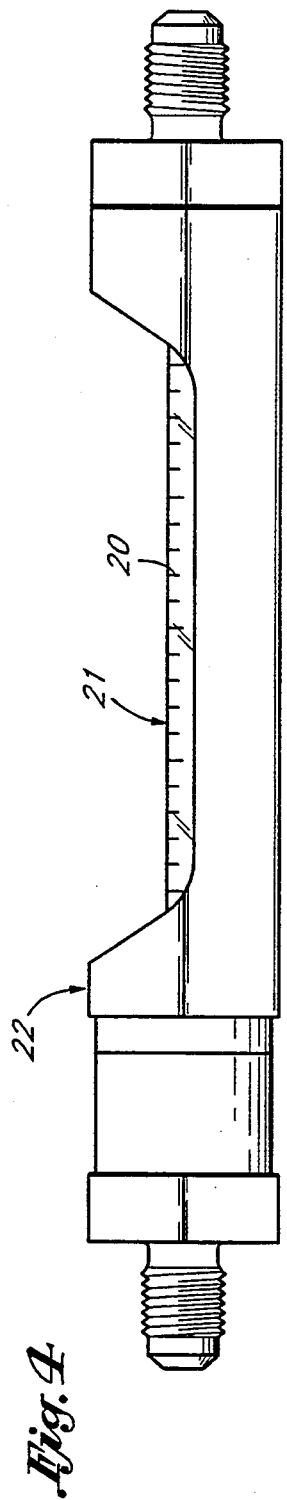
FIG. 4 is a side view of the detector tube holding assembly of FIG. 2.

The refrigerant gas contamination detector kit of the present invention is shown as part of an assembly in FIG. 1 and indicated generally by reference character 10. Kit 10 is connected to a tank 11 of a refrigerant of unknown contamination. The refrigerant in tank 11 is partly in a liquid phase and partly in a gaseous phase. A contaminant such as water will be displaced at equilibrium between the liquid phase and the gaseous phase and the relative amounts in each of these phases differs with different refrigerant gasses.

Figures 5, 6:
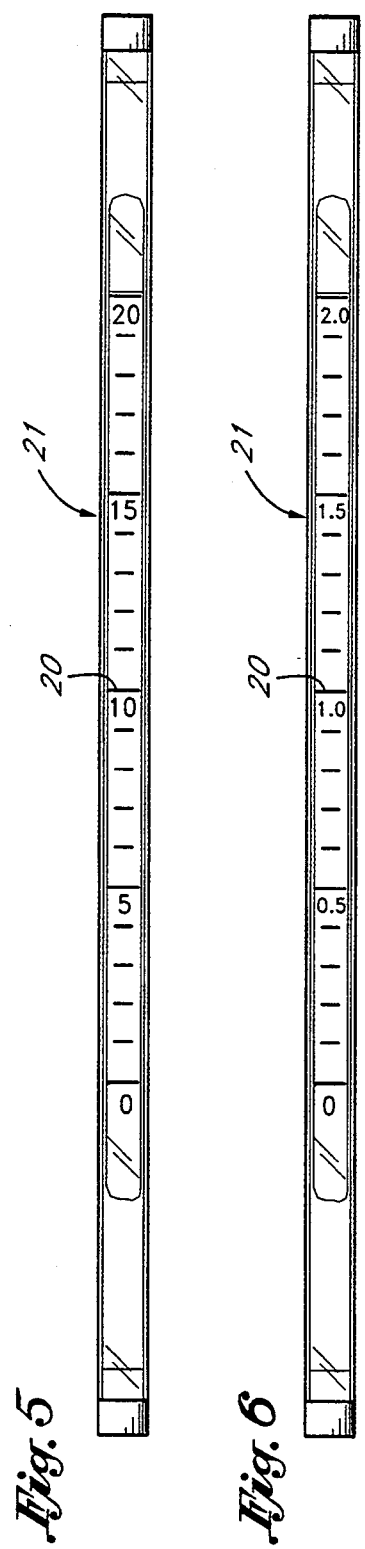
FIG. 5 is a top view of the detector tube of the detector tube holding assembly FIG. 2.
FIG. 6 is a top view of a detector tube analogous to that of FIG. 5.
Figure 7:
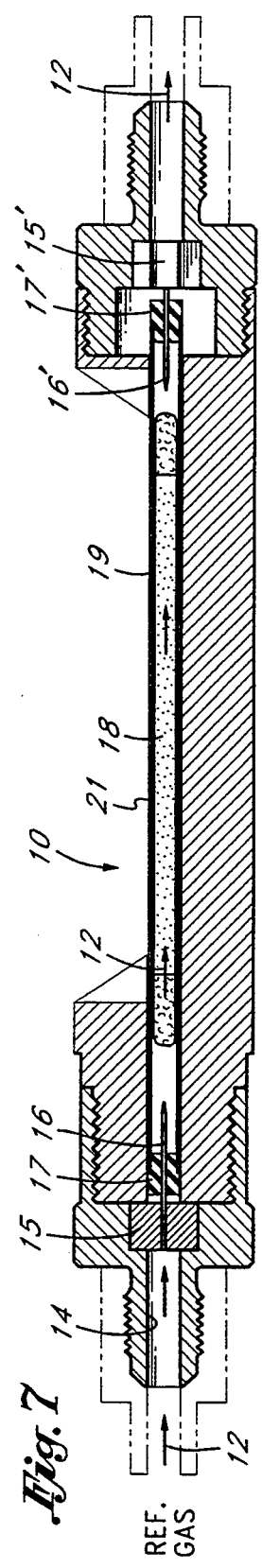
FIG. 7 is a cross-sectional view taken along line 7—7 of FIG. 2.

Experimentally, gas standards were composed to determine the required mass or gas volume necessary to render a true water and acid content reading. As shown best in FIG. 7, refrigerant gas 12, which passes through conventional fittings 13 from tank 11 passes through a threaded opening 14 through a disc 15, which supports a hypodermic needle 16. Hypodermic needle 16 has pierced a rubber stopper 17 and thus permits a refrigerant gas 12 to pass through a granular detector material 18 held in a transparent tube 19 which has marked indicia 20 shown in FIGS. 5 and 6 on the upper surface thereof. The refrigerant gas exits tube 19 through hypodermic needle 16' which has pierced rubber stopper 17'. Hypodermic needle 16' is held in disc 15' and allows the refrigerant gas 12 to exit the kit 10.

It is preferred to sample the vapor phase as compared to the liquid phase, since the contaminant is more homogeneously dispersed in the vapor phase. For instance, liquid water may rest in a layer on top of the refrigerant liquid and thus if the liquid phase were sampled it would be very difficult to get a homogenous sample.

In order to calibrate the detector tube, a Teflon lined cylinder was thoroughly cleaned and evacuated. The Teflon lined cylinder was required in order to ensure against any unwanted internal surface absorption or reaction from the mixture. A 1,000 gram sample of an R-22 gas that contains 10 ppm water and from 0 to 10% of refrigerant grade mineral oil is placed in the Teflon lined cylinder and allowed to stabilize for 30 minutes. The inlet of a detector tube 21 containing a moisture sensitive reagent 18 is connected to the Teflon lined cylinder and the outlet of the detector tube is connected to a pre-weighed cylinder. The gas flow is charted until the linear color change of the detector tube reagent reaches a length of one inch. The amount of sample gas sent through the tube is weighed. The same procedure is repeated for each type of refrigerant gas.

Next 1.0 ppm of hydrochloric acid is added to 1,000 grams of a known refrigerant and a detector tube containing an acid indicating reagent is placed in the holder 22 shown in FIG. 3. Holder 22 has an elongated slot 23 to permit viewing of the indicia 20 of detector tube 21. The mixture is again allowed to stabilize for 30 minutes and the gas flow is allowed to pass through the detector tube until the color change reacts to a length of one inch. The amount of sample gas passed through the tube is weighed.

It was noted that when refrigeration oil was added up to 10% no deviation in the color change lengths were observed. In fact the presence of oil intensified the degree of color change but not the length of color stain. Some acid detector tubes of the prior art incorporate a water removal, cleansing layer or demister before the indicating layer and such an arrangement greatly reduced the sensitivity of the acid indicator reagent and further caused inconsistent readings with the more highly fluorinated refrigerants. Detector tubes having breakable glass tips are not appropriate since they instantly allow air and moisture to enter the vial and precontaminate the indicating layer before the refrigerant gas is sampled.

The method of the present invention permits the withdrawal of a small sample of gas from a refrigeration system or tank where a typical two-phase gas liquid state is at or near equilibrium. The stable gas state allows for calibration against known standards in order for the test to be considered valid and verifiable. The present invention establishes a principle wherein a prescribed mass of gas is allowed to pass through a direct reading dosimeter style detection tube or vial. The indicating layer of the detection tube will react with a linear color change in a proportional amount to a target contaminant. The gas mass/volume is a specific quantity, which is substantially different for each refrigerant gas type being tested.

Hypodermic needles 16 and 16' are of a non-coring pencil point tip having a side hole. As shown best in FIG. 3, holder 22 has female threads 24 on the exit end and male threads 25 on the inlet end. The exit fitting 26 is tightly secured to holder 22 and a detector tube 21 (either a moisture sensing detector tube or an acid sensing detector tube) is inserted into elongated slot 23. A rubber stopper 17' abuts hypodermic needle 16' after which the entrance fitting 27 is threaded on to male threads 25, which both pierces stopper 17 and also stopper 17'. The fittings 13 of FIG. 1 have been flushed of air when the piercing takes place and thus only refrigerant gas will enter the detector tube. The hypodermic needles not only pierce the rubber stopper but also tend to slow down the flow of gas to a more manageable rate. Exit fitting 26 is connected to a volumetric measuring device, mass meter, pressure gauge, pressure hose gauge manifold, transducer, recorder or scale.

The mass and/or volume of gas allowed to pass through a dosimeter-type detection tube is critical. Each refrigerant type will hold a different but definite percentage of contaminants dissolved in both the vapor and liquid phase. If the vapor phase is sampled, then only the contaminants in that phase will react and the unreacted contaminants in the liquid phase must be determined from a known ratio. Differential ratios of contaminant distribution have been determined experimentally and found to have affinities peculiar to each refrigerant gas type. Since the contaminant ratio remains constant in a stable fluorocarbon gas, the mass and/or volume of the test gas must be varied to yield equivalent color stain progression from a single composition detector tube. Otherwise it would be necessary to develop a detector tube specifically for each refrigerant gas.

The manipulation of gas mass/volume through a single composition tube is paramount to the calibration of a direct reading indicating layer. Initially, acid and moisture reactions were determined; however, the standardization methodology can be extended to cover additional target contaminants or compounds.

The outlet of the apparatus has an important provision for the connection to a common service hose gauge manifold indicated generally by reference character 30 in FIG. 1. This hose gauge manifold has a 3-foot length of hose 31 connected through a valve having a handle 32 which passes into valved manifold 33 to which a pair of pressure gauges 34 and 35 are held. A second three-foot length of $\frac{1}{4}''$ I.D. hose 36 is connected to manifold 33 and a third length 37 is also connected to manifold 33. This provides a total length of 9 feet of hose having a $\frac{1}{4}''$ internal diameter. The hose gauge becomes a receptacle that captures a known volume of test gas and is an apparatus or standard tool which a refrigeration technician would have readily available. Positive pressure gas flow passing out through the detection tube is thereby contained and a specific volume can be quantified as pressure builds within the hose/gauge manifold. The quantitative conversion of captured gas is expressed by way of a termination pressure chart or more simply defined as the pressure at which to cease flow, dismantle the apparatus, remove and read the results preserved by the detector tube. The termination pressure is different for all refrigeration gasses.

A sample termination pressure chart is given for both R-12 and R-22 when the indicating reagent of the detector tube is at a fixed concentration for either moisture or acid assays.

R-12 60 psig
R-22 100 psig

Standard deviation is + or −10% and allowable pressure variance is + or −2 psig. The following is a termination pressure chart for different refrigerant gasses.

| TERMINATION PRESSURE CHART ±2 PSIG Vapor phase | |
|---|---|
| Type | PSIG |
| R-12 | 60 |
| R-22 | 100 |
| R-134a | 30 - acid |

-continued

TERMINATION PRESSURE CHART
±2 PSIG Vapor phase

| Type | PSIG |
|---|---|
| | 55 - moisture |
| R-500 | 65 |
| R-502 | 120 |
| R-11 | 2 |
| R-123 | 1 |

Preferably the detector tube has a glass body and the plugs at each end are rubber. It is advantageous to color code the apparatus by utilizing, for instance, a blue color at the entrance end of the detector tube holder and a blue plug or rubber stopper 17 at the entrance end of the detector tube vial. In this way a service man may be easily guided to correctly assemble the kit for proper gas flow direction.

Traditional chemistries employ moisture absorbing desiccants such as silica gels, aluminum oxide, magnesium sulfate, sodium sulfate, calcium chloride, calcium sulfate, cobaltous chloride, cuprous chloride, etc. These desiccants can be coated with a pH indicating dye which will yield a color change from a base (alkaline) reaction as moisture is absorbed by the desiccant material, or an oxidation-reduction dye can be used to yield a color change from the chemical alteration in combination with moisture.

Another method for quantifying moisture in detection tubes is by using compounds that react exothermically with water such as with magnesium perchlorate, sodium metal, lithium aluminum hydrite, etc. The color reaction again can be distinguished with the use of a pH dye or an oxidation-reduction indicator (redox).

Both of the above mentioned detector tube media may also react with carbon dioxide, carbon monoxide, nitrogen oxides, oxygen and other gaseous by-products found in a refrigeration fluid. The quantification of moisture, therefore, in a refrigerant gas may include these components as a source of error.

A specific moisture sensitive antigen/chromophore, Resorufin (labeled) Galactopyranoside, is coated onto dry glass beads and packed into a detector tube the indicator remains colorless until hydrolyzed to a red-violet end point.

The preferred acid indicator utilizes an enzyme. Many of the dehydrogenases, such as Formate Dehydrogenase, are enzymes that are potent antagonists to a wide variety of acidic products. When used as an acid detector material in combination with a redox dye such as Brilliant Creysl Blue, the reacted media releases carbon dioxide turning the indicating media from blue to white. These indicators exhibiting a vivid color change, provide an easy to read detector tube. Of course, other indicators known to those skilled in the art can be used.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A method for making a detector tube for determining the amount of a specific contaminant in a group of commonly used refrigerant gases, which gases also exist in a liquid phase comprising:

sealing a known detector material in a sealed transparent tube, said detector material being sensitive to a known contaminant;

transferring a known volume of a pure sample of one of said groups of commonly used refrigerant gases to a container having an outlet valve under sufficient pressure to cause said sample to exist in both liquid and gaseous phases within said container, said sample being a captured sample;

preparing a flow path between said captured sample, through said sealed tube of detector material, to a volume measuring unit;

contaminating said pure sample with a known amount of the contaminant to which the detector tube is sensitive producing a known contaminated sample;

waiting a time sufficient for the contaminant in the known contaminated sample to reach equilibrium between the liquid and the gaseous phase in said container;

opening said outlet valve on said container of contaminated sample and permitting a portion of the gaseous phase of said contaminated sample to pass through the transparent tube until the detector material has reached a predetermined distance in the detector tube;

measuring the weight of gas which is required to cause said detector material to reach a predetermined distance; and repeating all steps for each of said group of commonly used refrigerant gases.

2. A detector tube holding assembly for holding an indicator tube for testing a property of a refrigerant gas comprising:

a slotted central receptacle having a threaded opening at an inlet end and a threaded opening at an exit end and a slot along a side thereof and an elongated passageway passing from said threaded opening at an inlet end and said threaded opening at an exit end and said slot extending into the elongated passageway;

a hypodermic needle having a sharpened end supported in a disk adjacent the inlet end and said sharpened end oriented toward the slotted central receptacle;

a threaded opening at the exit end of said slotted central receptacle, said threaded opening having a central passageway passing therethrough leading to the elongated passageway of said central receptacle; and a piercing fitting having thread means which mate with the threaded opening at the exit end of said slotted central receptacle, said piercing fitting having a hypodermic needle supported thereby axially oriented so that a sharpened point of said hypodermic needle is threadingly moved into the central passageway of said threaded opening at the exit end of said slotted central receptacle, said piercing fitting having a threaded exit fitting with a central opening therein whereby when a detector tube having rubber ends and a transparent central portion is placed in the elongated passageway of said slotted central receptacle and the piercing fitting is screwed onto the threaded opening of the slotted central receptacle, the two hypodermic needles will pierce any rubber ends of such detector tube and permit refrigerant gas to pass through the detector tube.

3. The holding assembly of claim 2 further including a detector tube having an elongated glass body having two open ends filled with detector granules and having a piercible rubber plug at each open end.

4. A refrigerant gas contaminant detector tube having an elongated cylindrical transparent body having an outer surface, said body being filled with granules of detector material and a flexible, gas impervious plug at each end and indicia on the outer surface thereof, said gas impervious plug not being rupturable by the pressure of refrigerant gas.

5. The refrigerant gas contaminant detector tube of claim 4 wherein said transparent tube is glass and the flexible gas impervious tubes are rubber.

6. The refrigerant contaminant detector tube of claim 4 wherein said detector material is captured in a center section of the elongated cylindrical transparent body by an inert, porous plug at each end of the detector material.

* * * * *